(12) United States Patent
Kipperman

(10) Patent No.: US 8,066,753 B2
(45) Date of Patent: Nov. 29, 2011

(54) SPECIALIZED CATHETER AND METHOD FOR PLACEMENT IN A BIFURCATED VESSEL

(76) Inventor: Robert Kipperman, Chatham, NJ (US)

( * ) Notice: Subject to any disclaimer, the term of this patent is extended or adjusted under 35 U.S.C. 154(b) by 106 days.

(21) Appl. No.: 12/350,564

(22) Filed: Jan. 8, 2009

(65) Prior Publication Data

US 2009/0163880 A1 Jun. 25, 2009

Related U.S. Application Data

(63) Continuation-in-part of application No. 11/428,934, filed on Jul. 6, 2006, now Pat. No. 7,824,438.

(51) Int. Cl.
*A61F 2/06* (2006.01)
(52) U.S. Cl. .................... 623/1.11; 623/1.35
(58) Field of Classification Search .............. 623/1.11, 623/1.35, 1.12, 1.23; 604/264, 103.04, 528; 600/585; 606/194, 108
See application file for complete search history.

(56) References Cited

U.S. PATENT DOCUMENTS

| | | | |
|---|---|---|---|
| 4,739,762 A | 4/1988 | Palmaz | |
| 5,759,191 A | 6/1998 | Barbere | |
| 5,895,406 A | 4/1999 | Gray et al. | |
| 5,922,021 A | 7/1999 | Jang | |
| 6,086,611 A | 7/2000 | Duffy et al. | |
| 6,120,536 A | 9/2000 | Ding et al. | |
| 6,179,856 B1 | 1/2001 | Barbere | |
| 6,254,593 B1 | 7/2001 | Wilson | |
| 6,379,383 B1 | 4/2002 | Palmaz et al. | |
| 6,387,120 B2 | 5/2002 | Wilson et al. | |
| 6,440,165 B1 | 8/2002 | Richter et al. | |
| 6,520,988 B1 | 2/2003 | Colombo et al. | |
| 6,796,976 B1 * | 9/2004 | Chin et al. | 604/523 |
| 6,923,829 B2 | 8/2005 | Boyle et al. | |
| 6,936,066 B2 | 8/2005 | Palmaz et al. | |
| 6,962,202 B2 | 11/2005 | Bell et al. | |
| 6,962,602 B2 | 11/2005 | Vardi et al. | |
| 7,037,332 B2 | 5/2006 | Kutryk et al. | |
| 2003/0187494 A1 * | 10/2003 | Loaldi | 623/1.11 |

(Continued)

OTHER PUBLICATIONS

Marco A. Costa et al., "Molecular Basis of Restenosis and Drug Eluting Stents," Circulation—Journal of the American Heart Association, cover page & pp. 2257-2273 (May 3, 2005) (downloaded from circ.ahajournals.org).

(Continued)

*Primary Examiner* — Ryan Severson
*Assistant Examiner* — Tin Nguyen
(74) *Attorney, Agent, or Firm* — Panitch Schwarze Belisario & Nadel LLP

(57) ABSTRACT

A specialized catheter is used in a method to place a stent assembly in a bifurcated vessel in an animal body, such as a human. Primary and secondary guidewires are inserted from a location external of the body through the primary vessel, the secondary guidewire being further inserted into a secondary vessel beyond a bifurcation area. The guidewires are inserted into a primary stent and catheter assembly such that the assembly can move along the guidewires to the bifurcation area where the primary stent is expanded. While retaining the secondary guidewire in the vessels, the primary catheter assembly and primary guidewire are removed, the secondary guidewire passing through specialized openings in the primary catheter. Then the secondary stent, mounted on a catheter, is passed through the primary vessel guided by the secondary guidewire, and into the secondary vessel. There, the secondary stent is expanded to form the bifurcated stent assembly in an efficient manner.

29 Claims, 7 Drawing Sheets

U.S. PATENT DOCUMENTS

| | | |
|---|---|---|
| 2004/0172121 A1 | 9/2004 | Eidenschink et al. |
| 2004/0186560 A1 | 9/2004 | Alt |
| 2005/0131530 A1 | 6/2005 | Darack |
| 2006/0100694 A1* | 5/2006 | Globerman ................. 623/1.35 |
| 2007/0135904 A1* | 6/2007 | Eidenschink et al. ....... 623/1.35 |

OTHER PUBLICATIONS

Office Action Issued Oct. 19, 2009 in U.S. Appl. No. 11/428,934.

* cited by examiner

SPECIALIZED CATHETER AND METHOD FOR PLACEMENT IN A BIFURCATED VESSEL

CROSS-REFERENCE TO RELATED APPLICATIONS

This application is a continuation-in-part of U.S. patent application Ser. No. 11/428,934, filed Jul. 6, 2006, now U.S. Pat. No. 7,824,438, issued Nov. 2, 2010, the entire disclosure of which is hereby incorporated herein by reference.

BACKGROUND OF THE INVENTION

The present invention relates to a specialized catheter and a method of placing the catheter and stents in a bifurcated vessel. More particularly, the method includes placing a primary stent in a primary vessel and a secondary stent in at least one secondary vessel which branches from the primary vessel, the secondary branch vessel(s) and the primary vessel forming at least one bifurcated vessel. The catheter is specialized to allow passage of a guidewire through the wall of the catheter and remove the primary stent assembly so that the secondary stent may be placed into position in the secondary vessel.

A stent, sometimes referred to as a graft, is an endoprosthetic device that is placed within or implanted in a tubular vessel, such as a vascular vessel like an artery or vein, or other vessel, such as intestine, esophagus or other tubular body organ in animals, and particularly humans, for treating blockages, stenoses or aneurysms of the vessel. The stent is implanted within the vessels to act as an internal scaffold or reinforcement to support collapsing, previously fully or partially occluded, weakened or abnormally dilated portions of the vessel wall. Typically, stents have been used to treat dissections in blood vessel walls, for example following balloon angioplasty of the coronary arteries and peripheral arteries, and to improve results of angioplasty by reinforcing the vessel wall. Stents also have been implanted in other body vessels, such as the gastrointestinal tract, particularly the urinary tract, the bile duct, the esophagus and the tracheo-bronchial tree to support weakened or otherwise damaged walls of those organs.

Typically, stents are elongated tubular products that have a first, unexpanded condition in which they are threaded through the appropriate body organs, such as blood vessels, by use of catheters and guidewires. Some stents are expanded by way of the use of a small balloon which is expandable by a fluid, such as a sterile saline solution, when the stent reaches the desired location. There are great number of examples of stents having various types of geometry, such as those disclosed in U.S. Pat. No. 4,739,762 of Palmaz (commercialized in various forms as the Palmaz stent), U.S. Pat. No. 5,895,406 of Gray et al. and U.S. Pat. No. 5,922,021 of Jang. Other types of stents have been developed that are made of materials, such as an alloy of nickel and titanium called nitinol, which, when initially compressed, are within the sheath of a catheter, are in an unexpanded state, but when released from the catheter sheath, self-expand to an appropriate degree without the use of a balloon to bear against the vessel walls and retain them in an open condition. A couple of examples of stents of this type are shown in U.S. Pat. No. 6,923,829 of Boyle et aL and U.S. Pat. No. 6,936,066 of Palmaz et al. Stents have been commercialized by Cordis Corp. (a Johnson & Johnson Company), Guidant Corp., Boston Scientific Corp., Medtronic Inc., all of the United States, and Medinol, Ltd. of Israel, among others.

The manufacture and installation of stents is a multi-billion dollar business which is increasing annually, particularly as populations age.

Some stents are drug-eluting stents by virtue of the material from which the stents are made having properties particularly relating to antithrombotic activity, or antirestenosis activity. Often during procedures relating to vessel repair or even the insertion of the stents, blood may form clots, resulting in potentially serious or fatal thromboses and, over time, scar tissue or other matter builds up in the vessels, often in the vicinity of and on, and even as a result of, the use of a stent, resulting in re-blockage or restenosis of the vessel. Drug-eluting stents, which may also include coatings, thin reservoirs containing leachable active ingredients, and other techniques, have been developed and are in use to help prevent or treat such thromboses or restenosis. Among a great many examples are drug-eluting stents of a type disclosed in U.S. Pat. No. 6,120,536 of Ding et al., or U.S. Pat. No. 7,037,332 of Kutryk et al., which discloses a device coated with an antibiotic that promotes adherence of endothelial cells to the device. Certain materials used in making stents are themselves antirestentotic or antithrombogenic, such as U.S. Pat. No. 6,379,383 of Palmaz et al.

The use of stents in relatively straight and unbranched vessels is fairly straightforward. Complications arise when the damage to be repaired is near or at ajunction or point of bifurcation in bifurcated vessels where a branch vessel joins a main vessel. There are difficulties in inserting stents both in the main or primary vessel and in the branched or secondary vessel, which may result in further damage to the vessel with increased risk of thrombosis and embolism or even additional perforation of the vessel. Complications that may arise are disclosed in U.S. Pat. No. 6,962,202 of Vardi et al., which discloses one type of apparatus and a method of using it for treating bifurcated vessels. Other examples of stents and methods of inserting them for use in bifurcated vessels are disclosed in U.S. Pat. No. 6,440,165 of Richter et al. and in U.S. Patent Application Publication No. US 2004/0186560, published Sep. 23, 2004. The disclosures of these and all other patents and publications mentioned herein are hereby incorporated herein by reference. Each of the patents or publication mentioned in this paragraph discloses alternative arrangements and methods of insertion. Despite the various techniques, there are still certain inefficiencies and concerns with the methods of inserting stent assemblies in bifurcated vessels. The present invention overcomes the difficulties in alignment and insertion of various types of stents.

The present invention provides a specialized primary stent catheter and the method of its use to positively and efficiently align and insert a stent assembly comprising a primary stent and a secondary stent into a bifurcated vessel. The stent may be a balloon-expandable stent or a self-expandable stent and may include a coating or be made of materials by which it may also be a drug-eluting stent. The stent is made of materials or includes imageable coatings or other markings to allow ready determination of its location within and passage through a vessel, which is particularly important when dealing with bifurcated vessels. Such coatings and technologies are well known to those skilled in the art. Substantially any type or configuration of stent may be used with the method of the present invention.

A portion of the primary catheter is separable so that after a primary guidewire guides the primary stent into a primary vessel, a secondary guidewire may be removed from the lumen of the primary catheter and guide a secondary stent into a secondary vessel. The separable portion of the catheter does not significantly protrude from a cross-section of the catheter, thus making the surface of the catheter less obtrusive as it travels through a vessel than would an external guide mounted on the body of the catheter.

The present invention provides for an improved catheter to guide the stent assembly into a bifurcated vessel, along with the method for placing the stent assembly into the bifurcated vessel, with complete stent support for the full bifurcated vessel, which reduces the risk of restenosis or other adverse consequences associated with treating bifurcated vessels.

BRIEF SUMMARY OF THE INVENTION

One aspect of the present invention relates to a method for placing a stent assembly in a bifurcated vessel in an animal body, the method comprising (a) locating and assessing an area in the body for placement of a stent assembly in a primary vessel and a secondary vessel at a location where the primary vessel and the secondary vessel intersect at a bifurcation area; (b) inserting a primary guidewire from a location external of the body through the primary vessel beyond the bifurcation area; (c) inserting a secondary guidewire from a location external of the body through the primary vessel and into the secondary vessel; (d) selecting a primary stent having a lumen, a side opening, a proximal end region and a distal end region, the primary stent being configured to fit within the primary vessel in the bifurcation area, and when expanded, to maintain patency of the primary vessel where the primary stent is installed; (e) mounting the primary stent on a primary stent catheter having a lumen and a side opening such that the primary stent is expandable when in position in the bifurcation area and the side opening of the primary stent is aligned with the side opening of the primary stent catheter; (f) inserting the primary guidewire through the lumen of the primary stent catheter surrounded by the distal end portion of the primary stent and extending through the lumen of the primary stent catheter surrounded by the proximal end region of the primary stent; (g) inserting the secondary guidewire into the aligned side openings of the primary stent and the primary stent catheter and extending through the lumen of the primary stent catheter surrounded by the proximal end region of the primary stent; (h) passing the primary stent catheter through the primary vessel and into the bifurcated area for placement of the primary stent within the primary vessel; (i) expanding the primary stent to maintain patency of the primary vessel in and adjacent to the bifurcation area, such that the side opening in the primary stent is aligned with the secondary vessel; (j) withdrawing the primary stent catheter and, optionally, the primary guidewire from the primary vessel, while retaining the secondary guidewire in the primary and secondary vessels; (k) selecting a secondary stent having a lumen, a proximal end region and a distal end region, the secondary stent being configured to fit within the secondary vessel in the bifurcation area, and when expanded, to maintain patency of the secondary vessel where the secondary stent is installed; (l) mounting the secondary stent on a secondary stent catheter having a lumen such that the secondary stent is expandable when in position through the side opening of the primary stent in the bifurcation area and when in position in the secondary vessel; (m) inserting the secondary guidewire into the secondary stent catheter lumen beginning from a portion surrounded by the distal end region of the secondary stent and extending through the lumen of the secondary stent catheter surrounded by the proximal end region of the secondary stent; (n) passing the secondary stent catheter through the primary vessel, through the proximal end region and side opening of the expanded primary stent into the bifurcated area for placement of the secondary stent within the secondary vessel and in fluid communication with the expanded primary stent; (o) expanding the secondary stent to maintain patency of the secondary vessel such that the proximal end region of the secondary stent is in fluid communication and in contact with the side opening of the expanded primary stent; and (p) withdrawing the secondary stent catheter and the secondary guidewire, and the primary guidewire if the primary guidewire was not previously withdrawn, from the secondary and primary vessels to a location external of the body.

Another aspect of the present invention relates to a catheter comprising a tubular body, a lumen extending through the tubular body, a proximal end of the tubular body, a distal end region terminating at a distal end of the tubular body opposite the proximal end, the tubular body having a separable portion at the distal end region adapted to allow passage of a guidewire within the lumen to be removed from the distal end region through the separable portion, a first side opening in the tubular body, and a second side opening in the tubular body, the second side opening being located between the first side opening and the separable portion and adapted for threading the guidewire from the distal end into the lumen under the separable portion, out of the second side opening over a portion of the tubular body, into the first side opening and into the lumen through the proximal end.

Yet another aspect of the invention relates to a method for placing a stent assembly in a bifurcated vessel using the aforementioned specialized catheter, the method comprising: (a) locating and assessing an area in the body for placement of a stent assembly in a primary vessel and a secondary vessel at a location where the primary vessel and the secondary vessel intersect at a bifurcation area; (b) inserting a primary guidewire from a location external of the body through the primary vessel beyond the bifurcation area; (c) inserting a secondary guidewire from a location external of the body through the primary vessel and into the secondary vessel; (d) selecting a primary stent having a lumen, a first side opening, a proximal end region and a distal end region terminating at a distal end of the primary stent, the primary stent being configured to fit within the primary vessel in the bifurcation area, and when expanded, to maintain patency of the primary vessel where the primary stent is installed; (e) mounting the primary stent on a primary stent catheter, the primary stent catheter having a tubular body, a lumen extending through the tubular body, a proximal end of the tubular body, a distal end region terminating at a distal end of the tubular body opposite the proximal end, the tubular body having a separable portion at the distal end region, a first side opening in the tubular body, and a second side opening in the tubular body, the second side opening being located between the first side opening and the separable portion, such that the primary stent is expandable when in position in the bifurcation area and the first side opening of the primary stent is aligned with the first side opening of the primary stent catheter; (f) inserting the primary guidewire from the distal end of the tubular body through the lumen of the primary stent catheter surrounded by the distal end portion of the primary stent, extending through the lumen of the primary stent catheter surrounded by the proximal end region of the primary stent, and through the proximal end of the tubular body; (g) inserting the secondary guidewire through the distal end of the tubular body into the lumen under the separable portion, out of the second side opening of the primary stent catheter, over a portion of the tubular body, into the aligned first side openings of the primary stent and primary stent catheter, extending through the lumen of the primary stent catheter surrounded by the proximal end region of the primary stent, and through the proximal end of the tubular body; (h) passing the primary stent catheter through the primary vessel and into the bifurcated area for placement of the primary stent within the primary vessel to a point such that the primary guidewire and the secondary guidewire diverge and the secondary guidewire passes through the separable portion, thereby removing the secondary guidewire from the distal end region; (i) expanding the primary stent to maintain patency of the primary vessel in and adjacent to the bifurcation area, such that the first side opening in the primary stent is aligned with the secondary vessel; (j) withdrawing the primary stent catheter and, optionally, the primary guidewire from the primary vessel, while retaining the secondary guidewire in the primary and secondary vessels; (k) selecting a secondary stent having a lumen, a proximal end region and a distal end region, the secondary stent being configured to fit within the secondary vessel in the bifurcation area, and when expanded, to maintain patency of the secondary vessel where the secondary stent is installed; (l) mounting the secondary stent on a secondary stent catheter having a lumen such that the secondary stent is expandable when in position through the first side opening of the primary stent in the bifurcation area and when in position in the secondary vessel; (m) inserting the secondary guidewire into the secondary stent catheter lumen beginning from a portion surrounded by the distal end region of the secondary stent and extending through the lumen of the secondary stent catheter surrounded by the proximal end region of the secondary stent; (n) passing the secondary stent catheter through the primary vessel, through the proximal end region and first side opening of the expanded primary stent into the bifurcated area for placement of the secondary stent within the secondary vessel and in fluid communication with the expanded primary stent; (o) expanding the secondary stent to maintain patency of the secondary vessel such that the proximal end region of the secondary stent is in fluid communication and in contact with the first side opening of the expanded primary stent; and (p) withdrawing the secondary stent catheter and the secondary guidewire, and the primary guidewire if the primary guidewire was not previously withdrawn, from the secondary and primary vessels to a location external of the body.

Another aspect of the present invention relates to a balloon for expanding a first balloon-expandable stent, the balloon comprising a tubular balloon having a proximal end and a distal end, the balloon being capable of receiving within its tubular structure a guidewire for deployment of the first stent, the balloon further comprising a side opening closer to the distal end than the proximal end though which a second guidewire and a second stent may pass.

As used herein, the article "a," "an" or a singular component includes the plural or more than one component, unless specifically and explicitly restricted to the singular or a singular component. Thus, for example, reference to "a secondary vessel" means one or more than one secondary vessel that may be associated with a primary vessel as part of a bifurcated vessel.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 14B depicts a further enlarged view of the boxed area of FIG. 13A.

FIG. 15B depicts a further enlarged view of the boxed area of FIG. 15A.

FIGS. 16B-16E are further enlarged end elevation views of the primary stent catheter of the boxed area of FIG. 16A, wherein FIGS. 16B through 16E are schematic representations of alternative embodiments of a separable portion of the primary stent catheter embodiments of FIGS. 11A and 13.

FIG. 17 shows a side opening and an optional extension of the side opening to the distal end of the balloon.

DETAILED DESCRIPTION OF THE INVENTION

Figure 1:
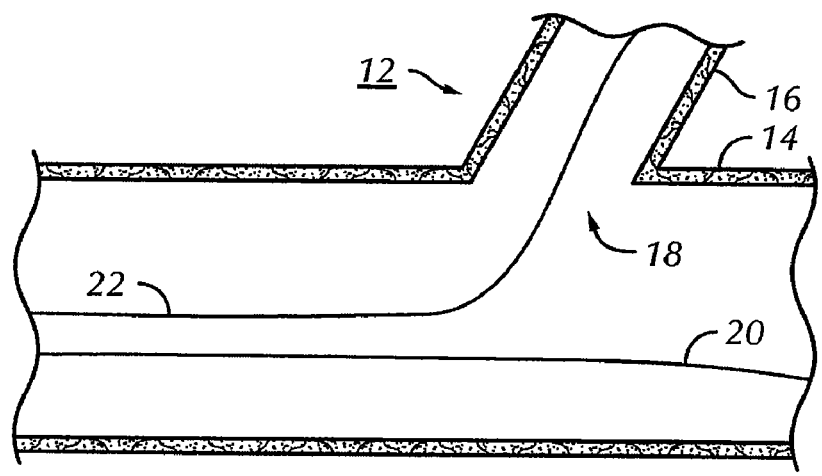
FIG. 1 is a schematic representation of a bifurcated vessel showing the insertion of primary and secondary guidewires therein as initial steps in the method of the present invention prior to the placement of the stent assembly in the desired location within a bifurcated vessel.

The present invention relates to various embodiments of catheters and methods of using them for placing a stent assembly in a bifurcated vessel in an animal body, preferably a human, where the vessels may be any type of bifurcated vessel as mentioned above, but particularly vascular vessels. Coronary vessels such as the aorta and its branches, renal arteries, great arch vessels such as subclavian, carotid and brachiocephalic vessels, are particularly preferred. Also, although the schematic depictions and descriptions herein relate to the insertion of a secondary stent into a single secondary vessel branching from a primary vessel, the same method may be applied to two or more branches extending from a primary vessel.

As mentioned above, any type of stent may be used, including stents of various geometry made of stainless steel, titanium, nitinol, nickel-chromium alloys, cellulose, and various synthetic polymeric plastics. Moreover, the primary and secondary stents used in the present method may be of any desired or appropriate dimension in view of the vessels in which they are to be inserted, but typically, without limitation, a primary stent has an expanded length of about 10 mm to about 40 mm, while a secondary stent typically, but without limitation, has an expanded length of about 5 mm to about 40 mm. The uses of the stents in particular vessels determine their diameter and length and the angle of the secondary stent with respect to the primary stent. For example without limitation, when the primary vessel is the aorta or a great arch vessel, the stents may have an expanded diameter of about 20 mm to about 50 mm. The branch vessels from the aorta are appropriately sized, and stents used therein may have an expanded diameter typically of about 4 mm to about 10 mm, while stents used in the secondary vessels from the great arch vessel typically may have an expanded diameter of about 8 mm to about 15 mm. Stents used in other coronary vessels typically may have an expanded diameter of about 2 mm to about 6 mm. Stents used with renal vessels typically may have an expanded diameter of about 4 mm to about 10 mm. The branched secondary vessels may intersect with a primary vessel at any angle. Such angle may vary, depending on the bifurcated vessels, such as at an angle of about 20° to about 120°, with typical angles being about 30°, about 45° and about 90°. Preferably, a number of stents and their associated catheters are prepared at different angles to be ready for insertion when appropriate.

Additionally, the primary or secondary stents may be drug eluting stents made of or coated with an antirestentotic or antithrombogenic material. Typically, but again without limitation, the antirestentotic material is an antimetabolite. Exemplary antirestentotic materials include paclitaxol, seruliomous, everulimous, antisense ribonucleic acid or nitric oxide, for instance. Non-limiting examples of antithrombogenic materials include heparin, enoxaprin, low molecular weight heparin, antithrombin, tissue plasminogen activator, streptokinase, urokinase and various antithrombogenic polymers. The materials may be coated either on the primary stent, the secondary stent, or both, and may be in the form of a polymer reservoir or matrix allowing for the gradual release of the material.

As also noted above, the stents used in the method of the present invention may be self-expandable or balloon-expandable. Although FIGS. 1, 5, 8, and 16A-16E are generic to all types of stents, for the purposes of clarity in illustrating and explaining this invention, FIGS. 2-4, 6, 7, and 11A-13B, are directed to the use of self-expandable stents, while FIGS. 9, 10, 13, 15A, 15B and 17 schematically depict the use of a balloon-expandable primary stent, where the principle would apply also to a balloon-expandable secondary stent, which is not illustrated specifically for the sake of clarity, but such stents are well known to those skilled in the art, and could be readily adapted to the present method without undue experimentation.

In addition to the description of the method illustrated in FIGS. 1 through 10, a specialized catheter and the method of its use will be described with respect to FIGS. 11A through 16. The specialized catheter depicted in FIGS. 11A through 16 functions similarly to the primary catheter in the stent assembly of FIGS. 1 through 10. For this reason, the last two digits of the identifying numerals of FIGS. 11A through 16 correspond generally to the last two digits of the identifying numerals in FIGS. 1 through 10.

Figure 8:
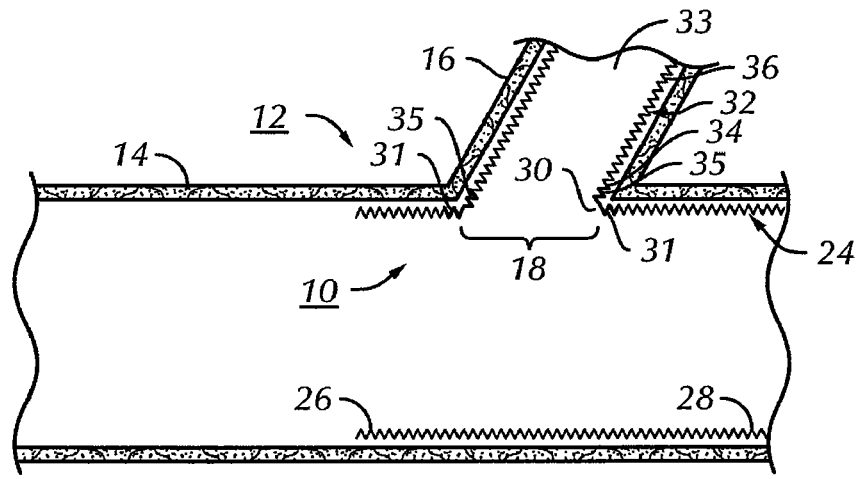
FIG. 8 schematically represents the placement of the expanded stent assembly within the bifurcated vessel after removal of the catheter assemblies and guidewires.

With reference to the drawings, wherein like numerals indicate like elements throughout the several views, there is shown in FIG. 8 a stent assembly 10 after insertion into a bifurcated vessel 12, which is also clearly shown in FIG. 1. The bifurcated vessel 12 includes a primary vessel 14 and at least one branch or secondary vessel 16 extending at any appropriate angle, such as about 20° to about 120°, with respect to the primary vessel 14. As noted above, for clarity and purposes of illustration, only one branch or secondary vessel 16 is illustrated, although two or more such secondary vessels, at any angles, could also be involved in the stent placement method according to the present invention. The primary vessel 14 and the secondary vessel 16 meet in a bifurcation area 18 best shown in FIGS. 1 and 8.

Again with reference to FIG. 8, and also with reference to FIGS. 2, 4, 6, and 11A, 11B, 12A and 12B, the stent assembly 10 includes a primary stent 24, 124 for expansion and implantation within the primary vessel 14, 114. The primary stent 24, 124 includes a primary stent lumen 25, 125, a proximal end region 26, 126, a distal end region 28, 128, and a distal end 29, 129. The embodiment of the primary stent 24 illustrated in FIGS. 2 and 4 includes a distal end region 28 and a side opening 30 between the proximal and distal end regions. The embodiment of the primary stent 124 illustrated in FIGS. 11A, 11B, 12A and 12B includes a first side opening 130 between the proximal end region 126 and the distal end 129.

The stent assembly 10 also includes a secondary stent 32, which may be identical in all embodiments of the present invention. As a result, FIGS. 11A through 16E do not show a separate secondary stent or a secondary catheter, since the secondary stent 32 and catheter may be used and placed within the secondary vessel 116 as described regarding the placement of the secondary stent 32 in the secondary vessel 32 with respect to the first embodiment regarding FIGS. 1-10. The secondary stent 32 has a lumen 33, a proximal end region 34, and a distal end region 36. The secondary stent 32 is implanted within the secondary vessel 16, 116 such that its lumen 33 is in fluid communication with the lumen 25, 125 of the primary stent 24, 124 through the side opening 30 (or first side opening 130) of the primary stent 24, 124. Preferably, as shown in FIG. 8, the end of the secondary stent 32 in the proximal end region 34 is in contact with the wall of the primary stent 24, 124 surrounding the side opening 30 (or first side opening 130). The side opening 30 (or first side opening 130) may be of any appropriate shape to correspond with the angle of the secondary stent 32 and the secondary stent 32 would have the appropriate shape to mate with the side opening 30 (or first side opening 130) in the primary stent 24, 124 to completely support the bifurcated vessels.

Although bifurcated stent assemblies are known in the art, the present invention relates to a more efficient and positive placement or insertion method with better alignment than is believed possible with prior art stent insertion methods resulting in a bifurcated stent assembly. Problems associated with such prior art insertion methods include the need to fish a secondary guidewire into the secondary lumen after the primary stent has been expanded, special shapes or angled portions of secondary stents, such as a flared proximal end portion, insertion methods which rely on the use of two balloons to expand a primary stent while aligning a primary stent opening with the lumen of the secondary vessel, and other problems, where insertion is difficult or uncertain and/or time-consuming. The more difficult and time consuming the procedure, the more the patient or other subject is at risk during and after the procedure. The insertion method of the present invention overcomes or at least reduces such problems and concerns.

With reference to FIG. 1, after an initial step of locating and assessing an area in the body for placement of a stent assembly in a primary vessel 14 and a secondary vessel 16 at a location where the primary vessel and the secondary vessel intersect at a bifurcation area 18, a primary guidewire 20 is inserted from a location external of the body through the primary vessel 14 beyond the bifurcation area 18. Typically, for certain coronary vessel angioplasty procedures and associated stent insertion procedures, insertion of the guidewires is through an incision in a femoral artery. A secondary guidewire 22 is also inserted from a location external of the body through the primary vessel 14 and into the secondary vessel 16. The insertion of the secondary guidewire 22 at the initiation of the procedure is an important aspect in assuring appropriate and accurate alignment of the secondary stent in the secondary vessel.

The remainder of the insertion method and further description of the specialized catheter will now be described with respect to an embodiment in which the stents are self-expandable stents inserted as schematically depicted in FIGS. 2-7, 11A, 12A, 14A, 14B and 16A-16E, resulting in the placement of the stent assembly 10 as shown and previously described with respect to FIG. 8.

After insertion of the guidewires as shown in FIG. 1, an appropriate primary stent 24, 124 is selected such that the primary stent side opening 30 (or first side opening 130) is appropriate in size and location with respect to the size and shape of the secondary vessel 16, 116 in the bifurcation area 18, 118 as determined by prior examination using various diagnostic or even exploratory surgical techniques. The stents used in the present invention are radio opaque or preferably have radio opaque or other suitable markings, such as marking 35, 135 at least at the proximal end region 34, 134 of the secondary stent 32, and optionally at the distal end region 36 (not shown) and, with respect to the primary stent 24, 124, markings 31, 131 in areas surrounding the side opening 30, (or first side opening 130), and optionally at the proximal and distal end regions 26, 126 and 28, 128. The markings, such as markings 31, 131 and 35 (although distal markings are not shown in the embodiment of enlarged FIGS. 11A through 16E), allow for the efficient travel and/or location of the stents in the body, and the secondary stent within the primary stent, so that they can be located and assessed by any suitable technique, such as fluoroscopy, plain radiography, arteriogram, virtual arteriogram, computerized tomography, magnetic resonance imaging, or any other appropriate technique. The primary stent 24, 124 is also configured to fit within the primary vessel 14, 114 in the bifurcation area 18, 118 and, when expanded, to maintain patency of the primary vessel 24, 124 where the primary stent is installed, as shown in FIG. 8.

The embodiment depicted in FIGS. 1 through 8 includes the primary stent 24 mounted on a primary stent catheter 38 having a lumen 40 and also a side opening 42 of a shape, size and location corresponding to the side opening 30 of the primary stent 24 so that the openings will be in alignment.

Figure 2:
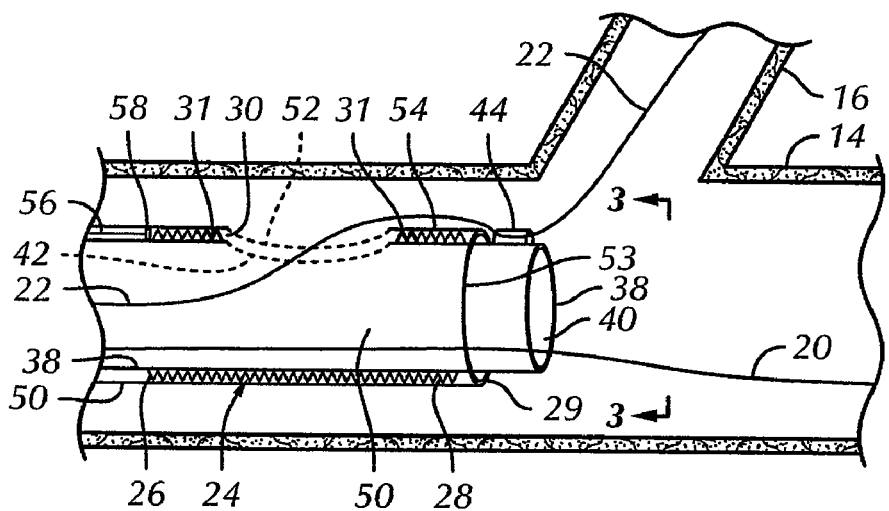
FIG. 2 is a schematic representation of a first embodiment of a primary catheter, sheath and stent assembly for inserting a self-expanding primary stent within the primary vessel in accordance with one embodiment of the method of the present invention.
Figure 3:
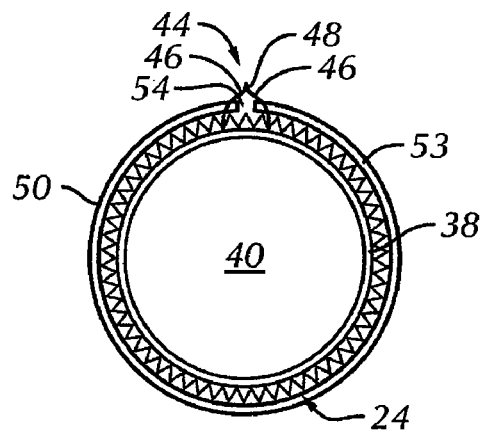
FIG. 3 depicts schematically an enlarged end elevation view of the primary catheter, sheath and stent assembly of FIG. 2 taken along lines 3-3 of FIG. 2.

As best shown in FIGS. 2 and 3, it is preferred, but not required, to use an optional peel-away wire guide 44 through which the secondary guidewire 22 is inserted, as explained below. The peel-away wire guide 44 includes side walls 46 attached to the surface of the primary catheter 38 at a location distal to the distal region 28 of the primary stent 24. The attachment may be by any sort of suitable nontoxic adhesive, melt bonding, fusion welding, etc. The peel-away wire guide 44 also includes a releasable closure member 48 of a type typically used in ZIP-LOK® reclosable plastic bags. Thus, for example, in this type of a releasable closure 48, a longitudinal male rib, with or without a small hook-like edge, is retained by friction within a longitudinal female groove with or without an interfitting hook edge reception slot for releasably retaining the peel-away releasable closure 48 in a closed condition upon pressing the components together. The releasable closure can be opened either by manually separating the releasable member components by pulling them apart, or by any other sufficient force which overcomes the friction created by the press fit arrangement of the releasable closure. The movement of a guidewire in a direction transverse to the longitudinal closure members is sufficient to cause the friction to be overcome to release the guidewire.

The embodiment depicted in FIGS. 11A through 16E includes the primary stent 124, mounted on a primary stent catheter 138 having a lumen 140, a separable portion 174 at the distal end region 178, a first side opening 142 of a shape, size and location corresponding to the first side opening 130 of the primary stent 124 so that the openings will be in alignment, and a second side opening 180, which may be in the form of a longitudinal slot, located between the first side opening 142 and the separable portion 174, the second side opening 180 defining the proximal end of the separable portion 174. The primary stent catheter 138 may also have a longitudinal slot 186, best seen in the alternative embodiments of FIGS. 11B and 12B, formed in an extension distal to the separable portion 174.

Figure 16A:
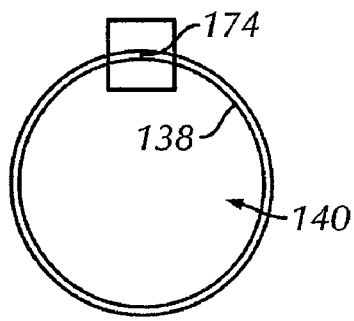
FIG. 16A depicts a schematically enlarged end elevation view of the primary stent catheter of FIGS. 11A and 13 taken along lines 16-16 of FIGS. 11A and 13.
Figure 16B:
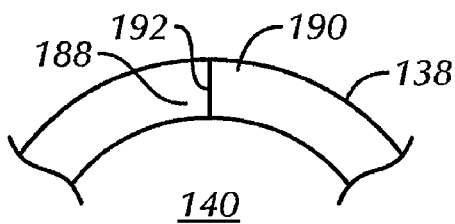
Figure 16C:
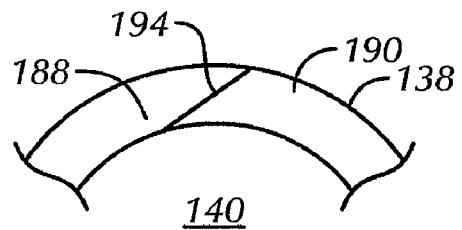
Figure 16D:
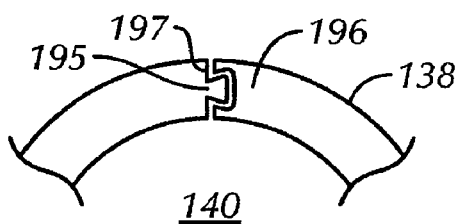

As best shown in FIGS. 14A and 16A through 16E, the separable portion 174 of the primary stent catheter 138 is contiguous with the circumference of the primary stent catheter 138. The preferred embodiment is depicted by FIG. 16D, in which the primary stent catheter 138 is split into a longitudinal male member 195 abutting a longitudinal female member 196, creating a releasable closure 197. In this embodiment, the releasable closure 197 is of a type typically used in ZIP-LOK® reclosable plastic bags. Thus, for example, in the releasable closure 197, the longitudinal male member 195 frictionally interlocks with the longitudinal female member 196 for releasably retaining the releasable closure 197 in a closed condition upon pressing the components together. The releasable closure 197 can be opened either by manually separating the releasable member components by pulling them apart, or by any other sufficient force which overcomes the friction created by the press fit arrangement of the releasable closure 197. The movement of a guidewire in a direction transverse to the longitudinal closure members is sufficient to cause the friction to be overcome to release the guidewire.

Figure 16E:
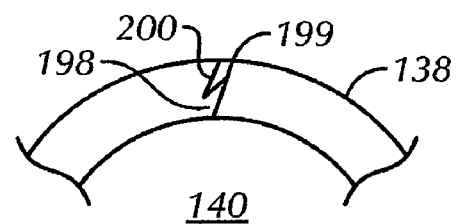

Alternative embodiments of the separable portion are depicted in FIGS. 16B, 16C, and 16E. FIG. 16B illustrates the primary stent catheter 138 being split into a longitudinal first portion 188 abutting a longitudinal second portion 190, creating a longitudinal slit 192. Another embodiment is shown in FIG. 16C, wherein the first portion 188 and second portion 190 abut each other in an overlapping longitudinal slit 194. Another type of releasable closure 200 is illustrated in FIG. 16E, in which the first portion 188 and second portion 190 are replaced by a hook portion 198 and a hook reception slot 199, respectively, in which the hook portion 198 is retained by friction within the interfitting hook reception slot 199.

Since the initial embodiment of the primary stent 24, 124 is a self-expandable stent, to prevent the stent from expanding away from the surface of the catheter 38, 138, a primary stent sheath 50, 150, having a distal end 53, 153 at the distal region 28, 128 of the primary stent 24, 124, as well as an opposed proximal end (not labeled) surrounds the primary stent 24, 124. The primary stent sheath 50, 150 also includes a side opening 52, 152 of the same size, shape and location as the side openings 30 and 42 (or first side openings 130 and 142) in the primary stent 24, 124 and the primary stent catheter 38, 138, respectively, all of such openings being in alignment.

The primary stent sheath 50, 150 also includes a longitudinal groove or slot 54, 154 in the surface of a portion of the primary stent sheath 50, 150 between the edge of the side opening 32, 132 and the distal end 53, 153 of the primary stent sheath. The groove 54, 154 is best seen in FIGS. 2, 3, 11A, 12A, 12B, 14A and 14B. The purpose of this groove 54, 154 is to allow the secondary guidewire 22, 122 to pass through the groove when the sheath 50, 150 is retracted to allow the self-expandable stent to expand.

In the embodiment illustrated in FIGS. 1 through 8, once the primary stent 24 is mounted on the primary stent catheter 38 and surrounded by the primary stent sheath 50, the primary guidewire 20 is inserted through the lumen 40 of the catheter 38, such that the primary guidewire 20 extends fully through the primary catheter, stent and sheath assembly. The secondary guidewire 22 is inserted at least into the aligned side openings 30, 42 and 52 of the primary stent 24, primary stent catheter 38 and primary stent sheath 50, respectively, and into the lumen 40 through the proximal end of the primary catheter, stent and sheath assembly. If the optional peel-away wire guide 44 is used, the secondary guidewire 22 is also threaded through it.

In the embodiment illustrated in FIGS. 11A through 16E, once the primary stent 124 is mounted on the primary stent catheter 138 and surrounded by the primary stent sheath 172, the primary guidewire 120 is inserted through the lumen 140 of the catheter 138, such that the primary guidewire 120 extends fully through the primary catheter, stent and sheath assembly. The secondary guidewire 122 is inserted through the distal end 129 of the primary stent catheter 138, into the lumen 140 under the separable portion 174 of the primary stent catheter 138, out of the second side opening 180 of the primary stent catheter 138, over a portion of the primary stent catheter 138, into the aligned first side openings 130 and 142 and the side opening 152 of the primary stent 124, primary stent catheter 138 and primary stent sheath 150, respectively, and extending through the lumen 140 through the proximal end of the primary stent catheter assembly.

After the primary guidewire 20, 120 and the secondary guidewire 22, 122 are inserted into the primary stent catheter 38, 138, the catheter and its associated primary stent 24, 124 and primary stent sheath 50, 150 are passed through the primary vessel 14, 114 along the primary guidewire 20, 120 and the secondary guidewire 22, 122 until the assembly reaches the bifurcation area 18, 118.

In the embodiment illustrated in FIGS. 1 through 8, at the point where the guidewires 20 and 22 diverge, as the primary catheter assembly is advanced along the primary guidewire 20 through the primary vessel 14, the secondary guidewire 22 will be released from the peel-away wire guide 44 if such guide is in use.

In the embodiment illustrated in FIGS. 11A through 16E, at the point where the guidewires 120 and 122 diverge, as the primary catheter assembly is advanced along the primary guidewire 120 through the primary vessel 114, the secondary guidewire 122 will be released from the lumen 140 of the primary stent catheter 138 through the separable portion 174.

Figure 4:
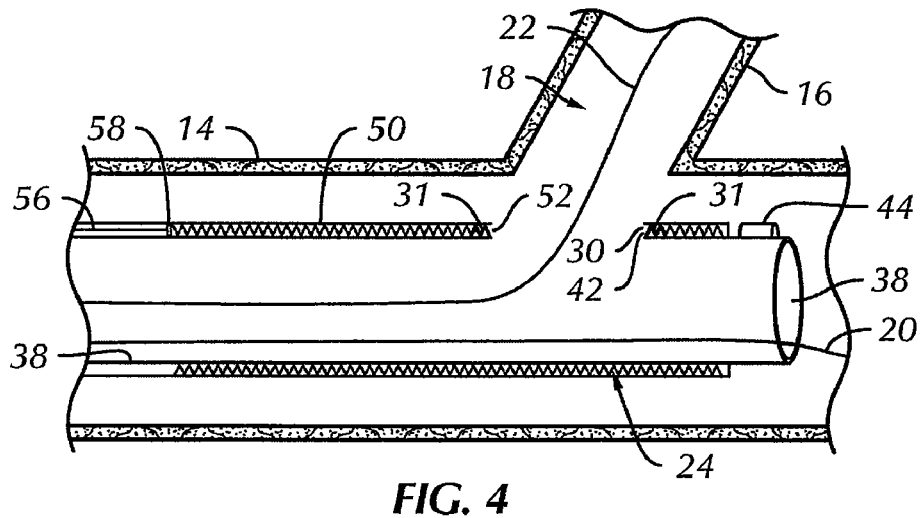
FIG. 4 schematically represents the alignment of the primary catheter, sheath and stent assembly of the first embodiment in the primary vessel such that the side openings in the primary stent catheter, the primary stent and the primary stent sheath are aligned with the opening to the secondary vessel in the bifurcation area prior to expansion of the primary stent in the primary vessel.
Figure 5:
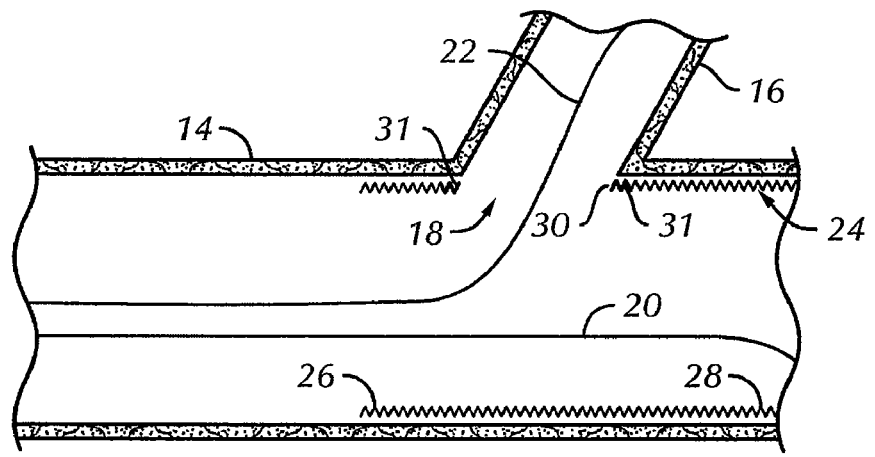
FIG. 5 schematically illustrates the placement of the primary stent within the primary vessel after the removal of the primary stent catheter assembly, but with the preferred retention of the primary guidewire, while retaining the secondary guidewire in place within the secondary vessel.
Figure 6:
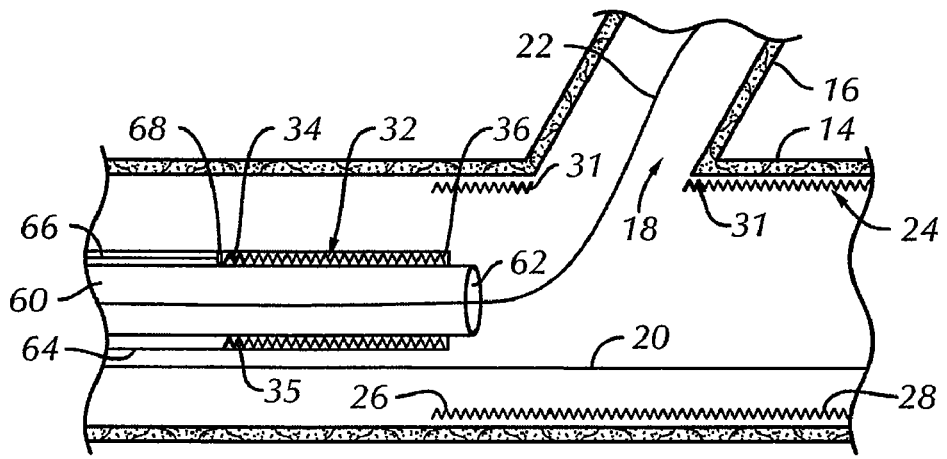
FIG. 6 schematically illustrates the insertion of an unexpanded self-expandable secondary stent on a secondary stent catheter and sheath assembly prior to insertion of the secondary stent into the secondary vessel.
Figure 7:
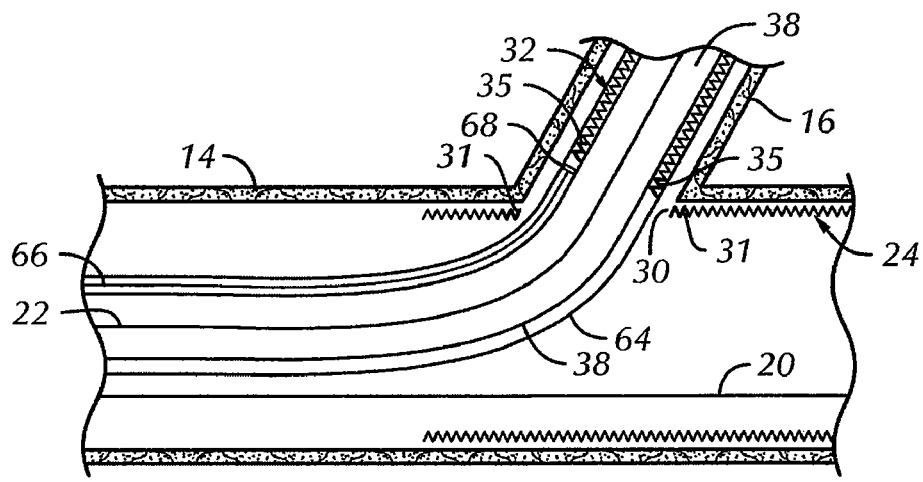
FIG. 7 schematically illustrates the insertion of the unexpanded secondary stent into the secondary vessel through the side opening in the primary stent.

In steps common to both embodiments of the present invention, the catheter assembly is then advanced to a location such that the side openings 30, 42 and 52 (or first side openings 130 and 144 and side opening 152) align with the secondary vessel 16, 116 in the bifurcation area 18, 118. At that time, the primary stent 24, 124 is inserted into position within the primary vessel 14, 114. Typically, this is accomplished by using a relatively stiff primary stent deployment wire 56, 156 located between the primary stent catheter 38, 138 and the primary stent sheath 50, 150. The primary stent deployment wire 56, 156 also has a distal primary stent deployment wire abutment member 58, 158 which abuts the proximal end of the primary stent 24, 124 to retain it in proper axial or longitudinal position on the catheter 38, 138 while withdrawing the primary stent catheter sheath 50, 150 from its retention position. When the sheath 50, 150 is withdrawn, by which the primary stent 24, 124 is retained on the catheter, the stent 24, 124 expands and bears against the walls of the primary vessel 14, 114, thus maintaining their patency. As the primary stent sheath 50, 150 is withdrawn out of the body, or at least off of the stent 24, 124, the secondary guidewire 22, 122 passes through the groove 54, 154 in the sheath 50, 150. The position of the primary catheter, stent and sheath immediately prior to the expansion of the primary stent 24 is shown in FIG. 4. Upon retraction of the sheath and the expansion of the primary stent 24, 124, the primary stent catheter 38, 138, the primary stent sheath 50, 150 and the primary guidewire 20, 120 all may be withdrawn from the primary vessel 14, 114, but the withdrawal of the primary guidewire 20, 120 may be, and preferably is deferred until the secondary guidewire 22, 122 is withdrawn and removed from the body as shown in FIGS. 5, 6 and 7. However, it is important that the secondary guidewire 22, 122 remain in the primary vessel 14, 114 and especially in the secondary vessel 16 as shown in FIG. 5.

Once the primary stent 24, 124 has been inserted in the primary vessel 14, 114 in the vicinity of the bifurcation area 18, 118, it is time to insert the secondary stent 32 into the secondary vessel 16, 116. This is accomplished by selecting a secondary stent 32 which is configured to fit within the secondary vessel 16, 116 in the bifurcation area 18, 118 and, when expanded, such secondary stent 32 maintains the patency of the secondary vessel 16, 116 when the secondary stent is installed and expanded. As best shown in FIG. 6, the secondary stent 32 is mounted on a secondary stent catheter 60 having a lumen 62. Since the embodiment shown in FIG. 6 is a secondary stent that is self-expandable, a secondary stent sheath 64 overlies the secondary stent 32 to keep it from expanding by itself.

The secondary guidewire 22, 122 is then inserted into the secondary stent catheter lumen 62 beginning from a portion surround by the distal end region 36 of the secondary stent 32 and extending through the lumen 62 of the secondary stent catheter 60 through the portion surrounded by the proximal end region 34 of the secondary stent 32. Thus, the secondary stent catheter, stent and sheath assembly are threaded onto the secondary guidewire 22, 122 and the assembly passes through the primary vessel 14, 114 until it reaches the bifurcation area 18, 118.

Upon reaching the bifurcation area 18, 118, as best shown in FIG. 7, the assembly travels along the guidewire 22, 122 through the side opening 30 (or first side opening 130) in the expanded primary stent 24, 124 and into the secondary vessel 16, 116. When the secondary stent, catheter and sheath assembly reaches the desired location within the secondary vessel 16, 116, the secondary stent 32 is deployed by allowing it to expand. This is accomplished in a manner similar to that described above with respect to the self-expandable primary stent 24, 124. Thus, a secondary stent deployment wire 66 having a secondary stent deployment wire abutment member 68 bears against the proximal end of the secondary stent 32, retaining it in the appropriate longitudinal position on the secondary stent catheter 38 while the secondary stent sheath 64 is withdrawn toward the body exterior, exposing the secondary stent 32 and allowing it to expand into the appropriate position as shown in FIG. 8. When properly inserted and expanded, the secondary stent 32 is in fluid communication with the expanded primary stent 24, 124, and preferably, the proximal end of the secondary stent 32 is in contact with the wall of the primary stent 24, 124 surrounding the side opening 30 (or first side opening 130) as shown in FIG. 8.

Figure 13:
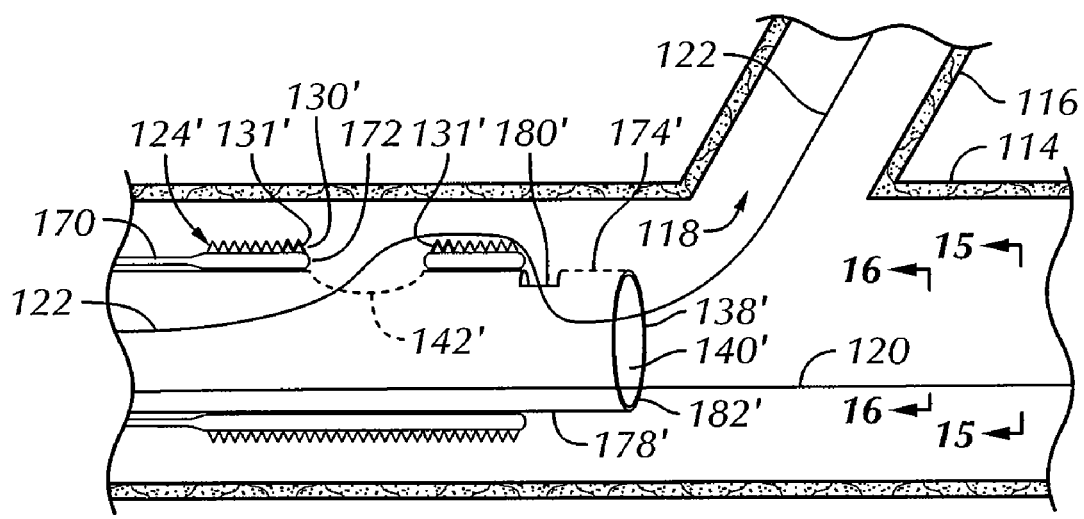
FIG. 13 is a schematic representation of an alternative embodiment of a primary stent catheter assembly for insertion of a balloon-expandable primary stent within the bifurcated vessel, prior to the expansion of the stent, using a second, alternative embodiment of a particularly constructed balloon as shown in FIG. 17 for the method of inserting primary and secondary stents in bifurcated vessels in accordance with the present invention.
Figure 14A:
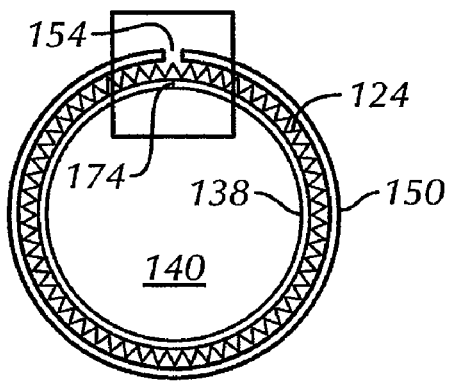
FIGS. 14A and 14B depict schematically enlarged end elevation views of the primary stent catheter assembly of FIG. 11A taken along lines 14-14 of FIG. 11A.
Figure 15A:
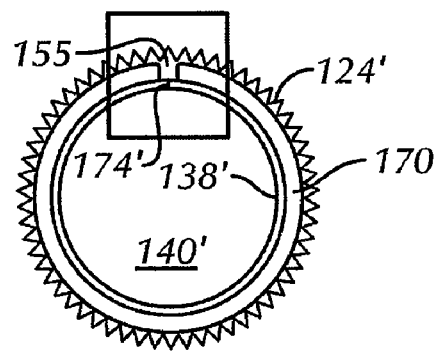
FIGS. 15A and 15B depict schematically enlarged end elevation views of the alternative embodiment of FIG. 13 taken along lines 15-15 of FIG. 13, depicting the distal end view of the alternative embodiment of a balloon as shown in FIG. 17.
Figure 14B:
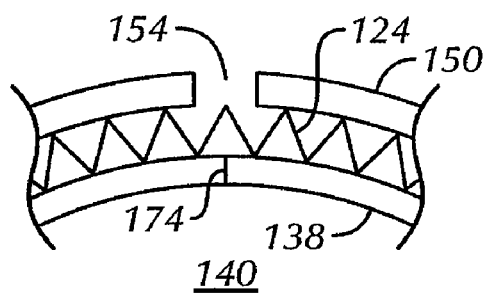
Figure 15B:
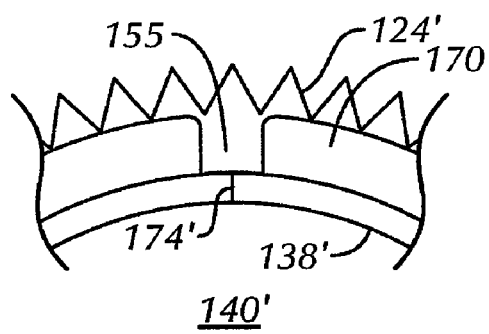
Figure 17:
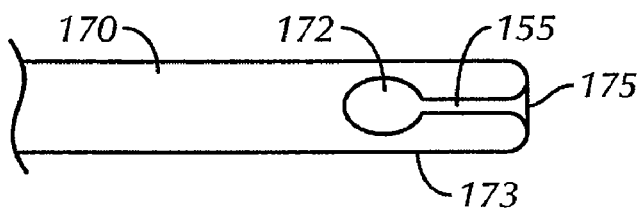
FIG. 17 is a schematic representation depicting a distal portion of an alternative embodiment of a balloon, in an plan view orientation rotated longitudinally 90° compared to the orientation of the balloon shown in FIG. 13, for use with a balloon-expandable primary stent in the method of the present invention for inserting primary and secondary stents in bifurcated vessels, where

The stent assembly 10 shown in its deployed, expanded position in FIG. 8, may be deployed using balloon-expandable stents, as well as by using self-expandable stents as described above. FIGS. 9, 13, 15A, and 15B depict a schematic representation of a primary balloon-expandable stent and catheter assembly with respect to the insertion of a balloon-expandable primary stent 24', 124', where the primed reference numerals identify the same elements as identified by the unprimed reference numerals of the embodiment shown in FIGS. 1-8, 11A, 12A, and 16A-16E as described above. The embodiments depicted in FIGS. 13, 15A and 15B show an assembly using an alternative embodiment of a balloon as best shown in FIG. 17, constructed for use in inserting a primary stent, 124' into the primary vessel 114, and a secondary stent (not shown but corresponding generally to stent 32, other than being balloon-expandable) into the secondary vessel 116, compared to a first balloon embodiment shown in FIG. 9. The method of placing a stent assembly in a bifurcated vessel using balloon-expandable stents is substantially the same as that described above with the following exceptions.

After locating and assessing an area in the body for placement of a stent assembly in a primary vessel 14, 114 and a secondary vessel 16, 116 where the primary and secondary vessels intersect at a bifurcation area 18, 118, the primary guidewire 20, 120 and the secondary guidewire 22, 122 are inserted into the vessels as described above and shown in FIG. 1. Then the appropriate balloon-expandable primary stent 24', 124' is selected and mounted on a balloon 70, 170, which in turn is mounted on the primary stent catheter 38', 138'. The balloon 70, 170 has a side opening 72, 172 closer to the distal portion 173 of the balloon than the proximal (not shown) portion or end of the balloon and that is at least of the same size and shape and that is aligned with the side opening 30' (or first side opening 130') in the primary stent 24', 124' and side opening 42' (or first side opening 142') formed in the primary stent catheter 38', 138'. The secondary guidewire 22, 122 and the secondary stent 32 extend through the side opening 72, 172 of the balloon 70, 170.

As shown in the alternative embodiment of FIGS. 13, 15A, 15B and 17, the side opening 172 may extend to the distal end 175 of the balloon 170. The distal extension of the side opening 172 may be simply the lack of balloon structure at a portion leading to the distal end 175 of the balloon 170 or the extension may be in the form of a space having a smaller transverse distance than the transverse distance of the side opening and of a dimension though which the guidewire is capable of passing that appears as a groove or slot 155 extending from the distal end 173 of the balloon to the side opening 172, as best seen in FIGS. 15A and 15B. The extension of the opening 72, 172 to the distal end allows the deployment of the primary stent 24', 124' without interfering with the secondary guidewire 22, 122, and enhanced retraction of the balloon 170 following the expansion of the primary stent 24', 124'. By forming a space in the form of a groove or slot 155 extending from the side opening 172 to the distal end 175 of the balloon 170, there is more balloon structure at the distal portion 173 that can be used to bear against and thereby expand the distal portion of the primary stent 124' when the balloon 170 is expanded. An optional sheath 50' including a groove 54', while not required where a balloon stent assembly is used, preferably is optionally used to protect the primary stent 24' and is shown as partially retracted in FIG. 9.

Figure 9:
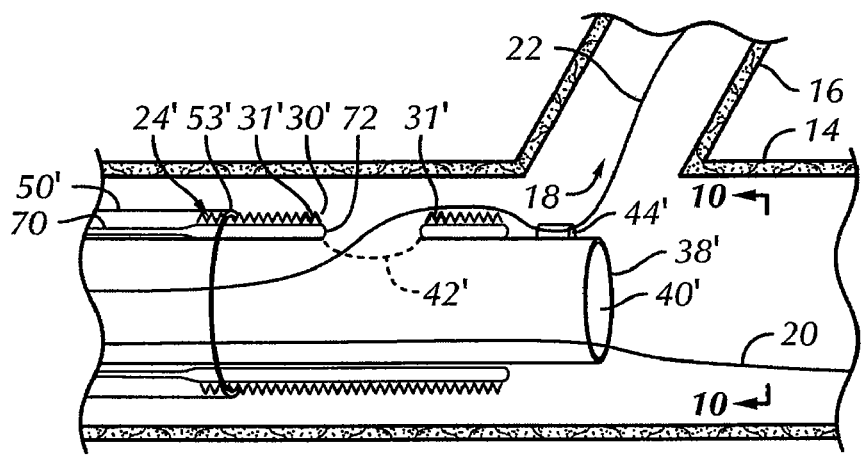
FIG. 9 is a schematic representation of an alternative embodiment of a primary stent catheter assembly for insertion of a balloon-expandable primary stent within the bifurcated vessel, prior to the expansion of the stent, using a first embodiment of a particularly constructed balloon for the method of inserting primary and secondary stents in bifurcated vessels in accordance with the present invention.
Figure 10:
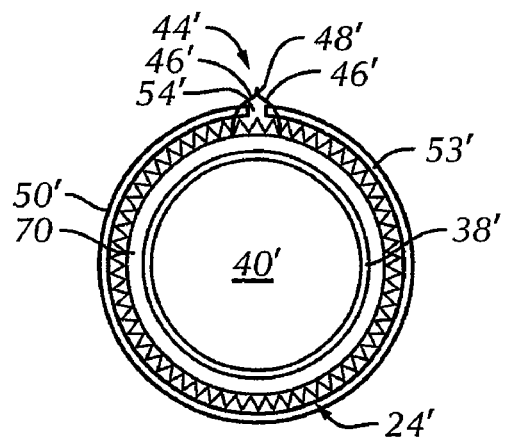
FIG. 10 depicts schematically an enlarged end elevation view of the primary catheter, sheath and stent assembly of the alternative embodiment of FIG. 9 taken along lines 10-10 of FIG. 9.
Figure 11A:
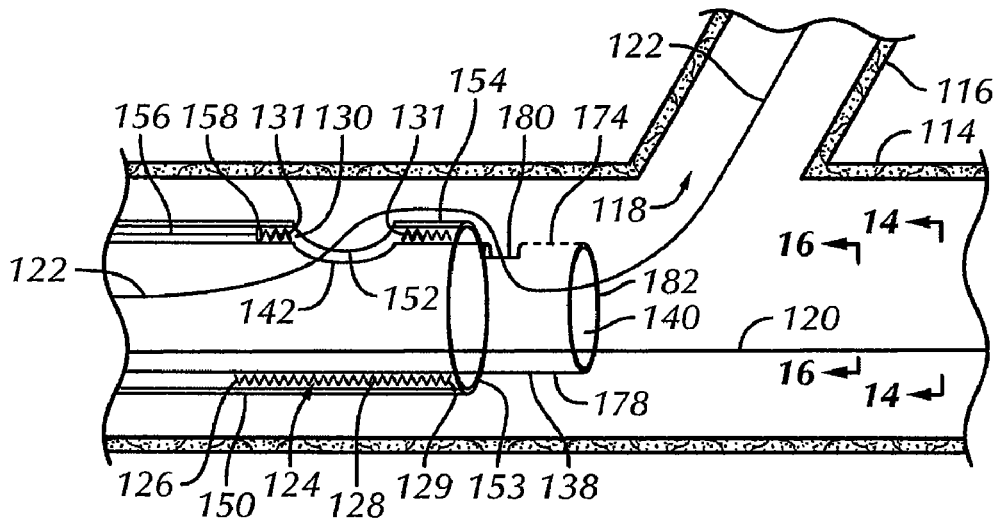
FIG. 11A is a schematic representation, in a side elevation view, of another alternative embodiment of a primary stent catheter assembly comprising a primary stent catheter, self-expandable primary stent, and primary stent sheath, for inserting the self-expandable primary stent within a primary vessel in accordance with another embodiment of the method of the present invention.
Figure 11B:
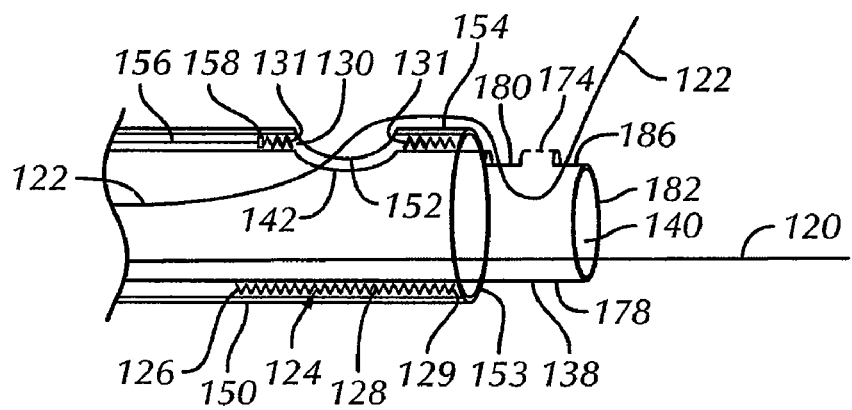
FIG. 11B is a schematic representation, in a side elevation view, of yet another alternative embodiment of a primary stent catheter assembly, for inserting the self-expandable primary stent within the primary vessel in accordance with an embodiment of the method of the present invention, wherein the primary stent catheter includes a first longitudinal slot.
Figure 12A:
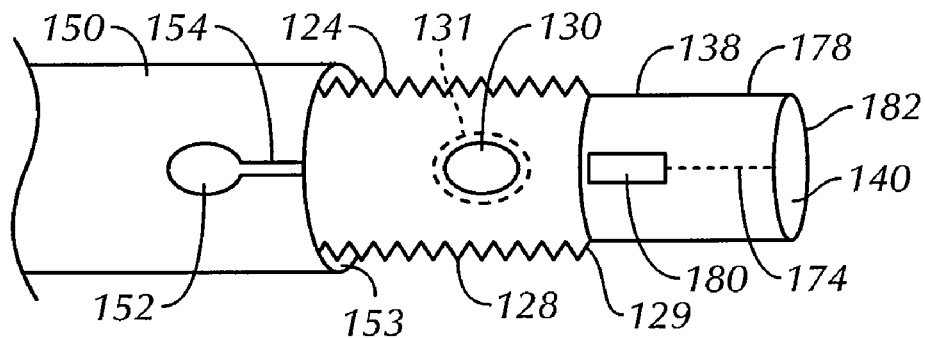
FIG. 12A is a schematic representation, in a top elevation view, of the embodiment of FIG. 11A of the primary stent catheter assembly wherein the self-expandable primary stent is partially exposed by the primary stent sheath.
Figure 12B:
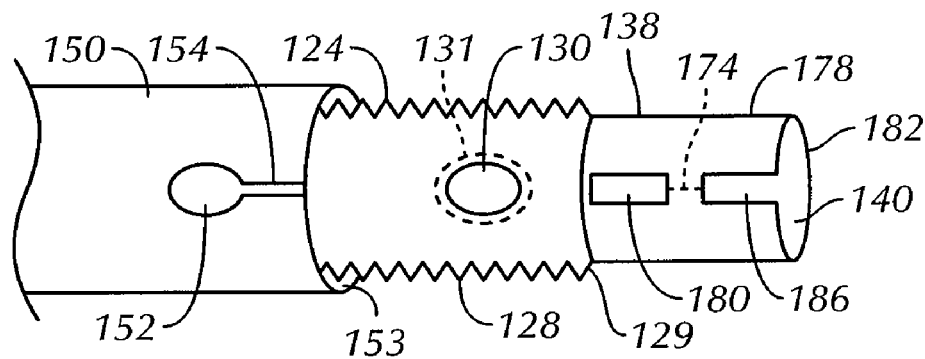
FIG. 12B is a schematic representation, in a top elevation view, of the embodiment of FIG. 11B of the primary stent catheter assembly wherein the self-expandable primary stent is partially exposed by the primary stent sheath.

In the embodiment depicted in FIGS. 1 through 10, after the primary balloon stent and catheter assembly shown in FIG. 9 has been assembled, the primary guidewire 20 extends into the lumen 40' of the primary stent catheter 38'. The secondary guidewire 22 is inserted either directly into the lumen 40' through the side openings 30', 42' and 72 or is threaded through the optional peel-away wire guide 44', before entering the lumen 40' through the side openings. Where a sheath 50' is used, the secondary guidewire 22 is also inserted into the side opening (not shown) of the sheath, as described above with respect to the first embodiment.

The primary balloon catheter assembly is then advanced along the guidewires 20 and 22 in the primary vessel 14 until the distal end reaches the bifurcation area 18. At that point, as described above with respect to the transition from FIGS. 2 and 4, where the primary guidewire 20 and the secondary guidewire 22 diverge, the secondary guidewire 22 is released from the peel-away wire guide 44' such that the side openings 30', 42' and 72 are in alignment with the secondary vessel 16.

In the embodiment depicted in FIGS. 11A through 16E, after the primary balloon stent and catheter assembly shown in FIG. 13 has been assembled, the primary guidewire 120 extends into the lumen 140' of the primary stent catheter 138'. The secondary guidewire 122 is inserted directly into the lumen 140' under the separable portion 174', out of the second side opening 180' of the primary stent catheter 138', over a portion of the primary stent catheter 138', into the first side openings 130', 142' and side opening 172 of the balloon 170, and through the lumen 140'.

The primary balloon catheter assembly is then advanced along the guidewires 120 and 122 in the primary vessel 114 until the distal end reaches the bifurcation area 118. At that point, as described above with respect to the transition from FIGS. 2 and 4, where the primary guidewire 120 and the secondary guidewire 122 diverge, the secondary guidewire 122 is released from the separable portion 174' such that the first side openings 130', 142' and side opening 172 are in alignment with the secondary vessel 116.

Common to both aspects of the invention, the primary balloon stent 24', 124' is then deployed by expanding the stent with pressure from the expanding balloon 70, 170 provided by an appropriate fluid, such as saline solution, such that the primary balloon stent 24', 124' would have the position shown for the self-expandable stent 24, 124 depicted in FIG. 5, to maintain the patency of the primary vessel 14, 114. Thereafter, the primary stent catheter 38', 138', the balloon 70, 170 may be withdrawn from the primary vessel 14, 114. While the primary guidewire 20, 120 may also be withdrawn at this stage, it is preferred to leave the primary guidewire 20, 120 within the primary vessel 14, 114, so as to leave the arrangement as shown in FIG. 5, where the primary stent 24', 124' has been expanded and deployed, the primary guidewire 20, 120 remains within the primary vessel 14, 114 and the secondary guidewire 22, 122 remains in the primary vessel 14, 114 and extends into the secondary vessel 16, 116.

A secondary balloon stent (not shown) is then mounted around a secondary balloon (not shown), which in turn is mounted on a secondary stent catheter (not shown). All of these components, while not shown in the drawings, are similar to the arrangement shown in FIG. 6 for the self-expandable catheter, stent and sheath assembly. Since a balloon catheter is being used, a secondary sheath is not required, but is also optional. The secondary guidewire 22, 122 is then threaded into a lumen in the secondary catheter and the secondary catheter and secondary stent assembly are moved along the secondary guidewire through the side opening 30 (or first side opening 130) in the expanded primary stent 24, 124 or 24', 124' into the bifurcation area 18, 118 and also into the secondary vessel 16, 116 for appropriate expansion as described above with respect to FIGS. 7 and 8, but using the balloon expansion technique described above with respect to FIGS. 9 and 13. The resulting expanded balloon secondary stent would then be installed in the secondary vessel 16, 116 to maintain the patency of the secondary vessel 16, 116 in communication with the primary stent as shown in FIG. 8.

The specialized stent catheter and the method of its use in the present invention for placing a stent assembly in a bifurcated vessel in an animal body is efficient and elegant, allowing for positive placement without overcrowding stents and catheters with excess balloons, external guides for the guidewire, and other components. By threading the primary stent assembly, including any catheter, balloon or sheath used therewith along both guidewires, and allowing for the release of the secondary guidewire 22, 122 from the distal end of the primary catheter and stent assembly through the separable portion 174 of the primary stent catheter 138, efficient and appropriate placement of the primary stent in the bifurcation area 18, 118 is accomplished readily. By removing the primary catheter assembly and any associated sheaths or balloons after the expansion of the primary stent, along with the removal of the primary guidewire 20, 120, the primary vessel is relieved of that apparatus. Yet by retaining the secondary guidewire 22, 122 in position within the primary vessel 14, 114 and the secondary vessel 16, 116, easy, efficient and positive location and alignment of the secondary stent 32 within the secondary vessel 16, 116 is accomplished readily by advancing the secondary stent and catheter assembly along the secondary guidewire into position passed the bifurcation area 18, 118 and into the secondary vessel 16, 116. This allows for the complete support of the bifurcated vessel 12, 112 by the primary stent 24, 124 and secondary stent 32, as shown in FIG. 8.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A catheter system comprising a catheter having a tubular body, a lumen extending through the tubular body, a proximal end of the tubular body, a distal end region terminating at a distal end of the tubular body opposite the proximal end, the tubular body having a separable portion at the distal end region; a guidewire passing within the lumen and removable transversely from the distal end region of the catheter through the separable portion; the catheter having a first side opening in the tubular body and a second side opening in the tubular body, the second side opening being located between the first side opening and the separable portion; the guidewire being threaded from the distal end of the catheter into the lumen under the separable portion, out of the second side opening over a portion of the tubular body, into the first side opening and out of the lumen through the proximal end.

2. The catheter system of claim 1, wherein the separable portion is longitudinally separable.

3. The catheter system of claim 1, wherein the second side opening is aligned with the first side opening.

4. The catheter system of claim 1, further comprising a first longitudinal slot which is distal to the separable portion and which extends to the distal end of the catheter.

5. The catheter system of claim 4, wherein the second side opening is a second longitudinal slot aligned with the first longitudinal slot.

6. The catheter system of claim 1, wherein the separable portion comprises a longitudinal slit in the tubular body.

7. The catheter system of claim 1, wherein the separable portion comprises a longitudinal first portion overlapping with a longitudinal second portion.

8. The catheter system of claim 1, wherein the separable portion comprises a longitudinal male member frictionally interlocking with a longitudinal female member.

9. The catheter system of claim 8, wherein the longitudinal male member has a longitudinal hook portion that is frictionally retained within a longitudinal female groove having a hook edge reception slot for receiving the longitudinal hook portion.

10. A method for placing a stent assembly in a bifurcated vessel in an animal body, the method comprising:

(a) locating and assessing an area in the body for placement of a stent assembly in a primary vessel and a secondary vessel at a location where the primary vessel and the secondary vessel intersect at a bifurcation area;

(b) inserting a primary guidewire from a location external of the body through the primary vessel beyond the bifurcation area;

(c) inserting a secondary guidewire from a location external of the body through the primary vessel and into the secondary vessel;

(d) selecting a primary stent having a lumen, a first side opening, a proximal end region and a distal end region terminating at a distal end of the primary stent, the primary stent being configured to fit within the primary vessel in the bifurcation area, and when expanded, to maintain patency of the primary vessel where the primary stent is installed;

(e) mounting the primary stent on a primary stent catheter, the primary stent catheter having a tubular body, a lumen extending through the tubular body, a proximal end of the tubular body, a distal end region terminating at a distal end of the tubular body opposite the proximal end, the tubular body having a separable portion at the distal end region, a first side opening in the tubular body, and a second side opening in the tubular body, the second side opening being located between the first side opening and the separable portion, such that the primary stent is expandable when in position in the bifurcation area and the first side opening of the primary stent is aligned with the first side opening of the primary stent catheter;

(f) inserting the primary guidewire from the distal end of the tubular body through the lumen of the primary stent catheter surrounded by the distal end portion of the primary stent, extending through the lumen of the primary stent catheter surrounded by the proximal end region of the primary stent, and through the proximal end of the tubular body;

(g) inserting the secondary guidewire through the distal end of the tubular body into the lumen under the separable portion, out of the second side opening of the primary stent catheter, over a portion of the tubular body, into the aligned first side openings of the primary stent and primary stent catheter, extending through the lumen of the primary stent catheter surrounded by the proximal end region of the primary stent, and out of the primary catheter lumen through the proximal end of the tubular body;

(h) passing the primary stent catheter through the primary vessel and into the bifurcated area for placement of the primary stent within the primary vessel, to a point such that the primary guidewire and the secondary guidewire diverge and the secondary guidewire passes transversely through the separable portion, thereby removing the secondary guidewire from the distal end region;

(i) expanding the primary stent to maintain patency of the primary vessel in and adjacent to the bifurcation area, such that the first side opening in the primary stent is aligned with the secondary vessel;

(j) withdrawing the primary stent catheter and, optionally, the primary guidewire from the primary vessel, while retaining the secondary guidewire in the primary and secondary vessels;

(k) selecting a secondary stent having a lumen, a proximal end region and a distal end region, the secondary stent being configured to fit within the secondary vessel in the bifurcation area, and when expanded, to maintain patency of the secondary vessel where the secondary stent is installed;

(l) mounting the secondary stent on a secondary stent catheter having a lumen such that the secondary stent is expandable when in position through the first side opening of the primary stent in the bifurcation area and when in position in the secondary vessel;

(m) inserting the secondary guidewire into the secondary stent catheter lumen beginning from a portion surrounded by the distal end region of the secondary stent and extending through the lumen of the secondary stent catheter surrounded by the proximal end region of the secondary stent;

(n) passing the secondary stent catheter through the primary vessel, through the proximal end region and first side opening of the expanded primary stent into the bifurcated area for placement of the secondary stent within the secondary vessel and in fluid communication with the expanded primary stent;

(o) expanding the secondary stent to maintain patency of the secondary vessel such that the proximal end region of the secondary stent is in fluid communication and in contact with the first side opening of the expanded primary stent; and (p) withdrawing the secondary stent catheter and the secondary guidewire, and the primary guidewire if the primary guidewire was not previously withdrawn, from the secondary and primary vessels to a location external of the body.

11. The method of claim 10, wherein the separable portion of the primary stent catheter is longitudinally separable.

12. The method of claim 10, wherein the second side opening in the primary stent catheter is aligned with the first side openings of the primary stent and primary stent catheter.

13. The method of claim 10, wherein the primary stent catheter further comprises a first longitudinal slot which is distal to the separable portion of the primary stent catheter and which extends to the distal end of the primary stent catheter.

14. The method of claim 13, wherein the second side opening is a second longitudinal slot aligned with the first longitudinal slot.

15. The method of claim 10, wherein the animal is a human.

16. The method of claim 15, wherein the bifurcated vessel is a vascular vessel.

17. The method of claim 16, wherein the vascular vessel is a coronary vessel.

18. The method of claim 10, wherein the primary stent is self-expandable, and wherein (e) of the method further comprises mounting the primary stent on the primary stent catheter and surrounding the mounted primary stent with a primary stent sheath having a distal end, a primary stent sheath side opening aligned with the first side openings of the primary stent catheter and the primary stent, and a longitudinal groove extending between the primary stent sheath side opening and a distal end of the primary stent sheath, whereby when the distal end of the primary stent sheath reaches a point of divergence of the primary guidewire and the secondary guidewire as the primary stent catheter passes through the primary vessel, the secondary guidewire passes through the groove to the aligned first side openings in the primary stent catheter and primary stent and the side opening in the primary stent sheath, and wherein (i) further comprises withdrawing the primary stent sheath to allow the primary stent to expand when in position in the bifurcation area.

19. The method of claim 18, wherein the secondary stent is self-expandable, and wherein (l) further comprises mounting the secondary stent on the secondary stent catheter and surrounding the mounted secondary stent with a secondary stent sheath, and wherein (o) further comprises withdrawing the secondary stent sheath to allow the secondary stent to expand when the secondary stent is in position within the secondary vessel.

20. The method of claim 10, wherein the primary stent is a balloon-expandable stent, and wherein (e) further comprises mounting the primary stent around a primary balloon which in turn is mounted on the primary stent catheter, the primary balloon having a primary balloon first side opening in alignment with the primary stent catheter first side opening and the primary stent first side opening, and wherein (i) further comprises expanding the primary balloon to expand the primary stent.

21. The method of claim 20, wherein the secondary stent is a balloon-expandable stent and wherein (l) further comprises mounting the secondary stent around a secondary balloon which in turn is mounted on the secondary stent catheter, and wherein (o) further comprises expanding the secondary balloon to expand the secondary stent.

22. The method of claim 10, wherein the secondary stent is inserted through the side opening of the primary stent, such that the secondary stent forms an angle of about 20° to about 120° with respect to the primary stent.

23. The method of claim 22, wherein the angle is about 30°.

24. The method of claim 22, wherein the angle is about 45°.

25. The method of claim 22, wherein the angle is about 90°.

26. The method of claim 10, wherein the primary stent has an expanded diameter of about 2 mm to about 50 mm, and the secondary stent has an expanded diameter of about 2 mm to about 15 mm.

27. The method of claim 26, wherein the primary stent has an expanded diameter of about 20 mm to about 50 mm, and the secondary stent has a diameter selected from the group consisting of about 2 mm to about 6 mm, about 4 mm to about 10 mm and about 8 mm to about 15 mm.

28. The method of claim 10, wherein the primary stent has an expanded length of about 10 mm to about 40 mm.

29. The method of claim 10, wherein the secondary stent has an expanded length of about 15 mm to about 40 mm.

* * * * *